(12) United States Patent
Woehr

(10) Patent No.: US 9,662,456 B2
(45) Date of Patent: May 30, 2017

(54) SAFETY SYRINGE

(75) Inventor: Kevin P. Woehr, Felsberg (DE)

(73) Assignee: B. Braun Melsungen AG, Melsungen (DE)

( * ) Notice: Subject to any disclaimer, the term of this patent is extended or adjusted under 35 U.S.C. 154(b) by 1580 days.

(21) Appl. No.: 12/595,668

(22) PCT Filed: Apr. 14, 2008

(86) PCT No.: PCT/US2008/060196
§ 371 (c)(1),
(2), (4) Date: Mar. 26, 2010

(87) PCT Pub. No.: WO2008/128157
PCT Pub. Date: Oct. 23, 2008

(65) Prior Publication Data
US 2010/0179487 A1     Jul. 15, 2010

(30) Foreign Application Priority Data
Apr. 13, 2007   (DE) .................... 20 2007 005 394 U

(51) Int. Cl.
*A61M 5/315*   (2006.01)
*A61M 5/32*    (2006.01)

(52) U.S. Cl.
CPC ........ *A61M 5/326* (2013.01); *A61M 5/31511* (2013.01); *A61M 5/31515* (2013.01);
(Continued)

(58) Field of Classification Search
CPC .. A61M 2005/3261; A61M 2005/3265; A61M 2005/3247; A61M 5/3257;
(Continued)

(56) References Cited

U.S. PATENT DOCUMENTS 3,939,833 A * 2/1976 Hansson ............ A61M 5/31511
604/202
5,267,976 A 12/1993 Guerineau et al.
(Continued)

FOREIGN PATENT DOCUMENTS

CN        1933861 A        3/2007
WO    WO 2004/045685      6/2004
WO    WO 2005/089831      9/2005

OTHER PUBLICATIONS

International Preliminary Report on Patentability mailed Oct. 22, 2009 from related International Application No. PCT/US2008/060196, filed Apr. 14, 2008 (6 pages).
(Continued)

*Primary Examiner* — Nathan R Price
*Assistant Examiner* — Weng Lee
(74) *Attorney, Agent, or Firm* — Klein, O'Neill & Singh, LLP

(57) ABSTRACT

Syringe assemblies are described with at least two co-axially positioned cylinders that move relative to one another by action of a spring. Aspects of the syringe assemblies include a protective unit in which a first cylinder of a first length is attached to a second cylinder of shorter second length. In different embodiments, a protective unit is formed of a single or singularly fabricated cylinder. The different protective units may be used with a syringe in which action of a plunger to push a plunger tip into contact with a distal wall of the syringe cylinder to discharge fluid located inside the syringe but does not immediately release the protective unit relative to the syringe cylinder to shield a needle.

3 Claims, 10 Drawing Sheets

(52) U.S. Cl.
CPC ............... *A61M 2005/3247* (2013.01); *A61M 2005/3261* (2013.01); *Y10T 29/49826* (2015.01)

(58) Field of Classification Search
CPC .. A61M 5/3219; A61M 5/3243; A61M 5/321; A61M 5/31511
See application file for complete search history.

(56) References Cited

U.S. PATENT DOCUMENTS

| | | |
|---|---|---|
| 5,342,309 A | 8/1994 | Hausser |
| 5,423,758 A | 6/1995 | Shaw |
| 5,433,712 A * | 7/1995 | Stiles .................... A61M 5/326 604/110 |
| 5,562,624 A | 10/1996 | Righi et al. |
| 6,093,170 A | 7/2000 | Hsu et al. |
| 6,206,853 B1 | 3/2001 | Bonnet |
| 6,679,864 B2 * | 1/2004 | Gagnieux et al. ............. 604/198 |
| 6,776,777 B2 * | 8/2004 | Barrelle ........................ 604/198 |
| 6,905,478 B2 | 6/2005 | Ingram et al. |
| 7,850,647 B2 * | 12/2010 | Ingram et al. ................ 604/110 |
| 2005/0096596 A1 * | 5/2005 | Crawford .............. A61M 5/326 604/198 |

OTHER PUBLICATIONS

International Search Report from related International Application No. PCT/US2008/060196 completed and mailed Sep. 25, 2008 (4 pages).
Written Opinion from related International Application No. PCT/US2008/060196 completed and mailed Sep. 25, 2008 (3 pages).
Office Action dated Jan. 18, 2012 from corresponding Chinese Application No. 200880019394.8 (10 pages).
Office Action dated Feb. 11, 2014 from corresponding R.O.C. (Taiwan) Application No. 97113464 (20 pages).

* cited by examiner

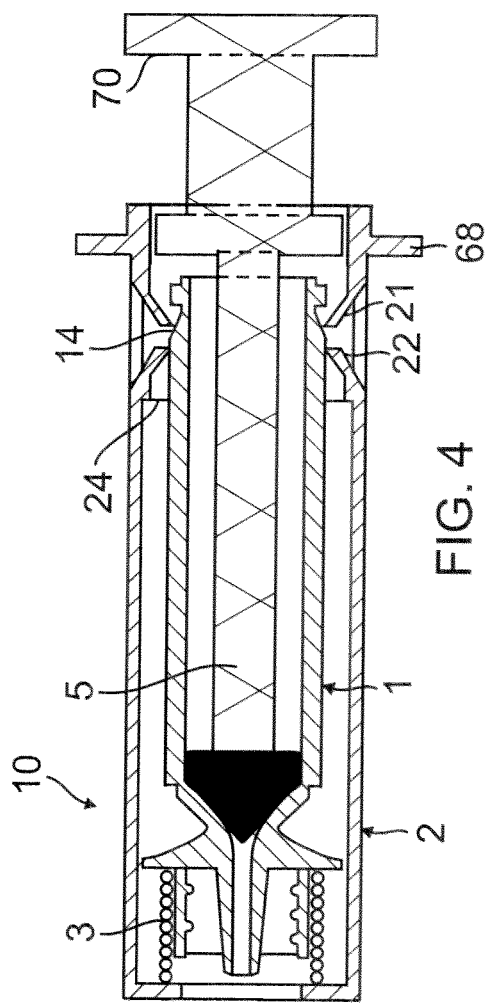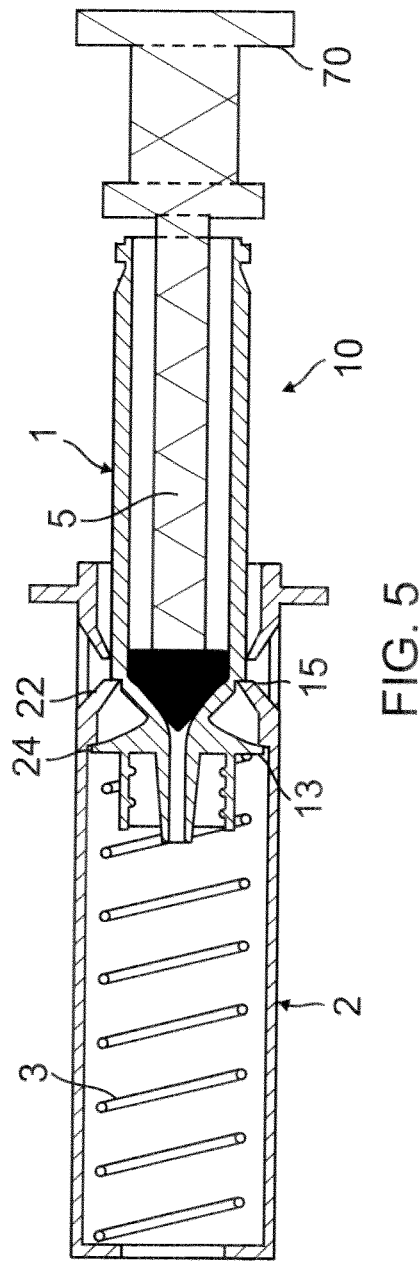

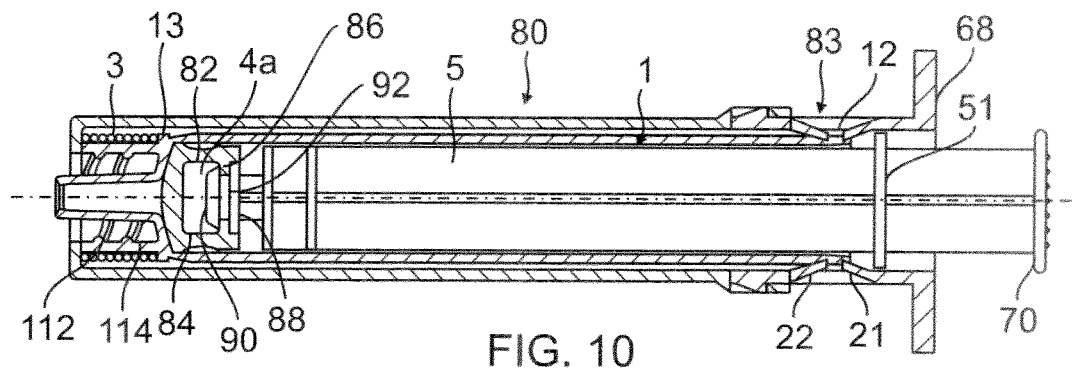
FIG. 10
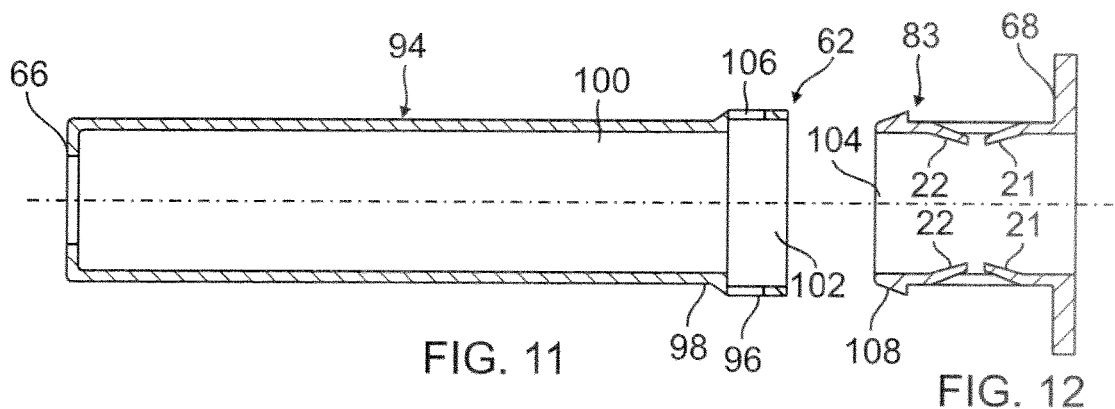
FIG. 11
FIG. 12
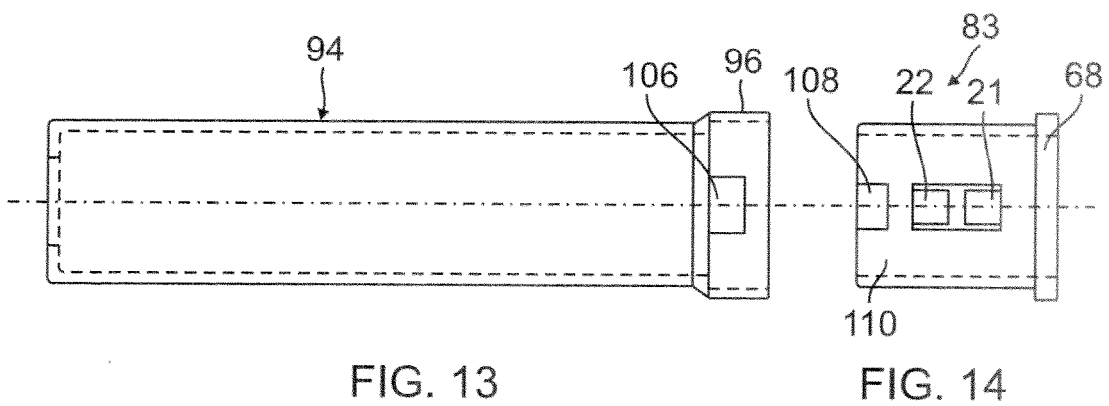
FIG. 13
FIG. 14

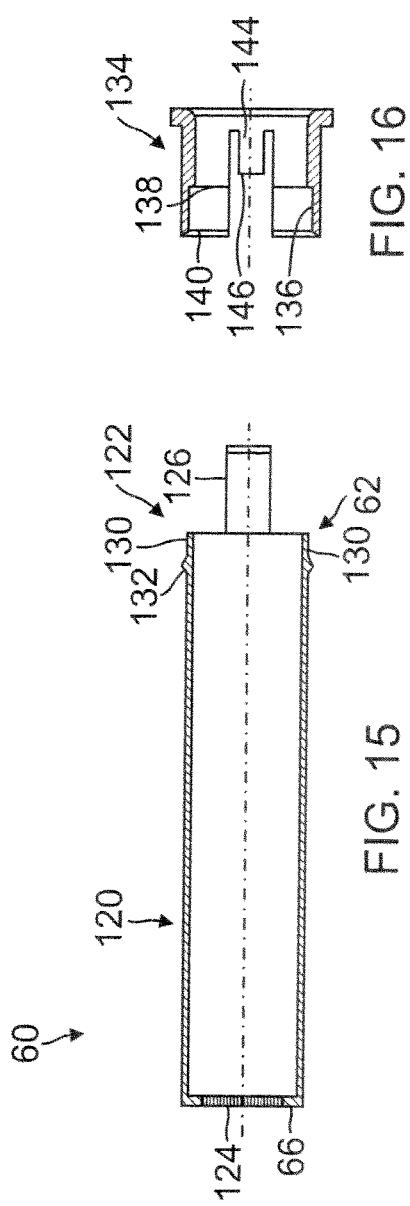
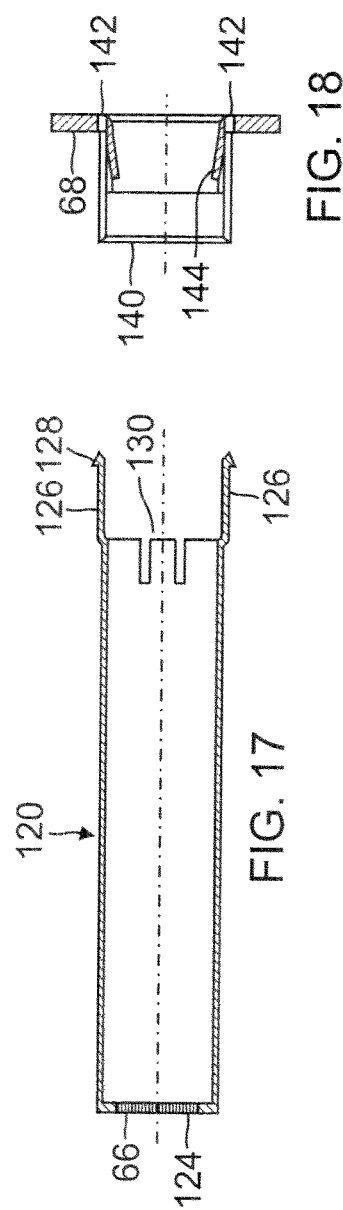
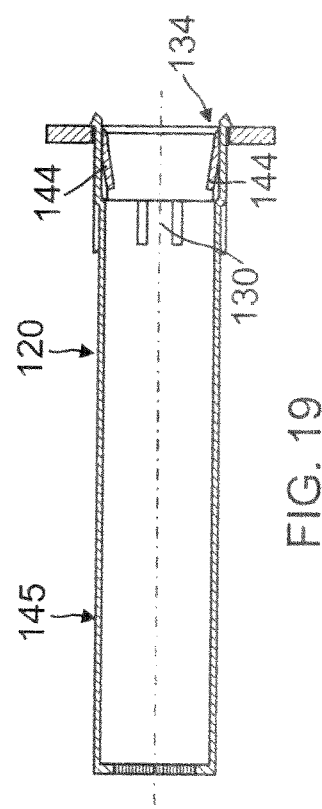

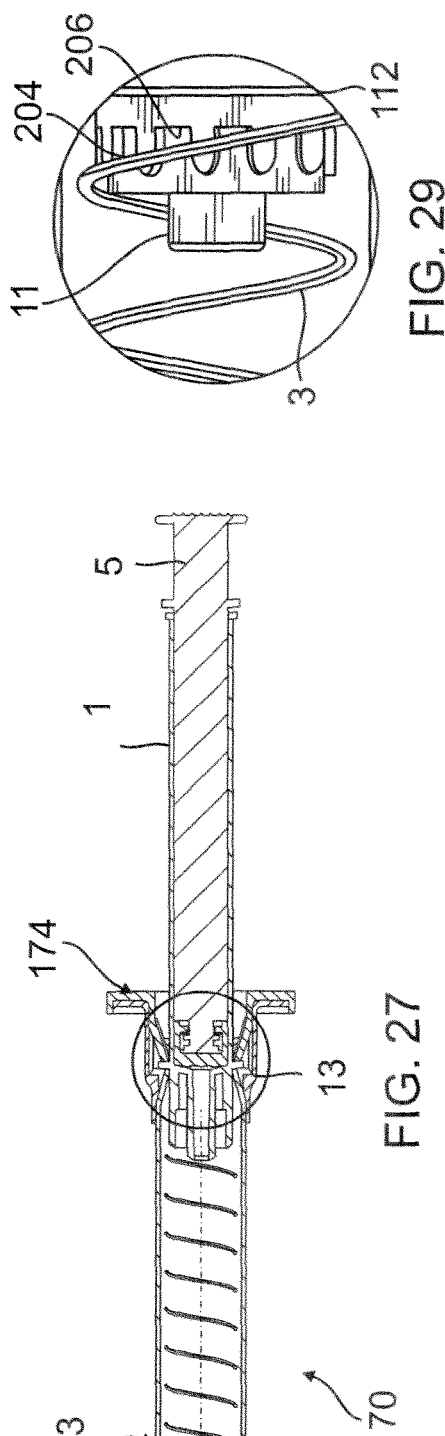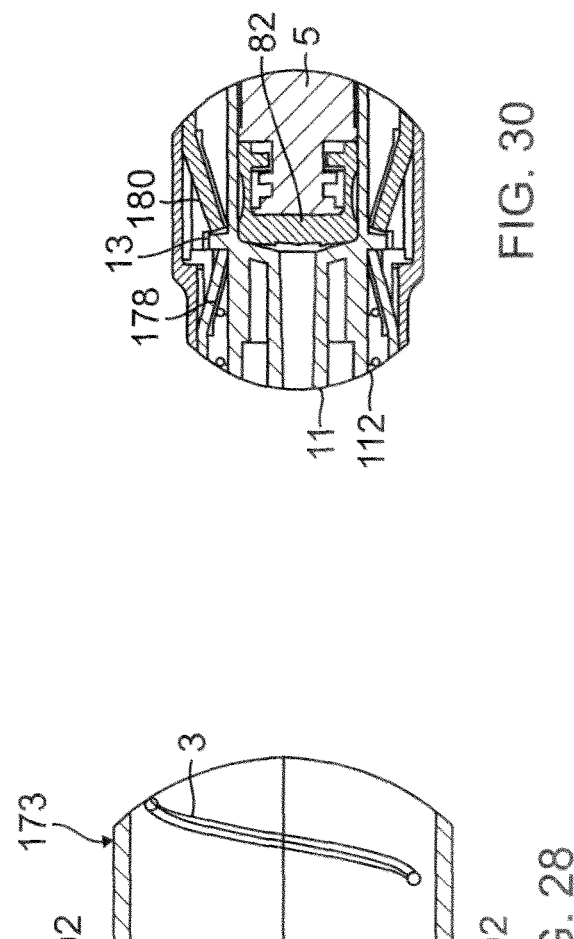

SAFETY SYRINGE

CROSS-REFERENCE TO RELATED APPLICATION(S)

This is a national stage application of PCT application No. PCT/US2008/060196, filed Apr. 14, 2008, which claims priority to German Utility Application No. DE 20 2007 005 394, filed Apr. 13, 2007, the contents of each of the foregoing are expressly incorporated herein by reference for all purposes.

BACKGROUND

Aspects of the present invention generally relate to a safety syringe and more particularly to a safety syringe that utilizes a spring loaded outer sheath.

Safety syringes are well known in the art, including from the teachings of WO 2005/089831. Before the syringe is put to use, the plunger disposed inside the barrel is in a starting position, which is a position in which the distal end of the plunger is spaced from the distal front wall of the syringe cylinder or barrel. For drawing up injection liquid, the plunger must first be moved in the distal direction in the syringe cylinder. However, moving the plunger too far distally will cause it to activate the safety mechanism. To limit this plunger movement in the distal direction, limiting arms are mounted at the proximal end of the plunger rod, and these cooperate with the proximal end of the protective cylinder surrounding the syringe cylinder such that the plunger can only be displaced up to just before its distal end position, wherein a small distance to its distal end position remains (FIG. 1). When the limiting arms come to bear at the protective cylinder, they are pivoted no that when an injection is carried out, they no longer prevent the full displacement of the plunger rod into the syringe cylinder, wherein the plunger can be displaced forward up to its distal end or used position at the front end of the syringe cylinder.

In this distal end position of the plunger, the catches at the proximal end of the syringe cylinder engage in recesses in the plunger rod, while they simultaneously release the connection between protective cylinder and the syringe cylinder so that a spring between the protective cylinder and the syringe cylinder displaces these with the plunger rod from the protective cylinder in a proximal direction, as soon as the plunger rod is released after carrying out the injection. Hereby, the needle at the syringe cylinder is drawn into a protective position in the protective cylinder, wherein further notches at the distal end of the syringe cylinder engage in recesses at the proximal end of the protective cylinder, so that the syringe cylinder with the needle can no longer be displaced out of the protective cylinder in the distal direction.

This construction with limiting arms on the one hand and notches at the distal and proximal ends of the syringe cylinder on the other is very complex. It is also deficient in that the design does not permit complete de-aeration of the syringe before drawing up injection liquid without the connection between protective cylinder and syringe cylinder being released (FIG. 1). Rather, the additional operating step of displacing the plunger rod inwards is necessary, which must be carried out contrary to the conventional use of a syringe. If this additional operating step were not carried out, the spring would not release at the end of the injection process.

SUMMARY

The present invention may be implemented by providing a safety syringe comprising a syringe cylinder in which a plunger rod with a plunger tip is displaceable, a protective cylinder which surrounds the syringe cylinder in a ready position, a spring means located between protective cylinder and syringe cylinder, which forces the two cylinders apart, and fingers located between a proximal end area of the syringe cylinder and the protective cylinder, through which the syringe cylinder is joined to the protective cylinder, and which is releasable by means of a plate at the plunger rod. In particular aspects of the present invention, when the plunger tip abuts the distal front wall of the syringe cylinder, a release movement of the plunger rod or of a part of the plunger rod is possible in the distal direction relative to the syringe cylinder, to release the fingers between syringe cylinder and protective cylinder.

In a further aspect of the present invention, a method is provided for securing a first cylinder to a second cylinder to form fingers for a syringe assembly. The method includes the steps of providing a protective cylinder comprising a radially inwardly projecting shoulder and one of a male detent and a female detent; providing a latching ring comprising a push flange, at least two distally facing fingers, and a corresponding one of a male detent and a female detent; securing the latching ring to the protective cylinder by mating the one of a male detent and a female detent on the protective cylinder with the corresponding one of a male detent and a female detent on the latching ring; providing at least two proximally facing fingers located distally of the at least two distally facing fingers; placing a syringe cylinder comprising a plunger rod and a plunger tip into the protective cylinder; and securing a flange on the syringe cylinder between the at least two proximally facing fingers and the at least two distally facing fingers to compress a spring.

In a further aspect of the present invention, a method for using a syringe assembly comprising a first cylinder secured to a second cylinder to form fingers is provided. The method comprising the steps of latching a latching ring to a protective cylinder to form a protective unit and wherein the protective unit is geared to a syringe cylinder to delimit relative rotation between the protective unit and the syringe cylinder; advancing a plunger rod into the syringe cylinder until a plunger tip contacts a distal wall of the syringe cylinder; and wherein a release flange located on the plunger rod is positioned proximally of the fingers and distally of a grip flange on the latching ring when the plunger tip contacts the distal wall.

In still yet further aspects of the present invention, a syringe assembly comprising a protective unit comprising a first cylinder of a first length attached to a second cylinder of shorter second length is provided. The assembly further includes a plunger rod comprising a plunger tip positioned inside a syringe cylinder, which is positioned inside the protective unit; a pair of proximally facing fingers and a pair of distally facing fingers located on the protective unit comprising a gap therebetween and having a flange on the syringe cylinder positioned in said gap. A gripping flange located on the second cylinder and proximally of the proximally facing and distally facing fingers is also provided and wherein a spring is compressed between a portion of the protective unit and a portion of the syringe cylinder.

In yet another aspect of the present invention, there is provided a method for securing a first cylinder to a second cylinder to form fingers for a syringe assembly. In one embodiment, the method comprises the steps of securing a coupler to the first cylinder and securing the second cylinder to the coupler so that the first cylinder is secured to the second cylinder; using the coupler to deflect a first finger on the first cylinder; using the coupler to deflect a second finger on the second cylinder; and wherein a flange on a syringe cylinder is held in a gap defined between the first finger and the second finger.

A still further aspect of the present invention is a syringe barrel comprising a coupler comprising a cylinder body section configured to compress a raised bump on a proximally facing finger and a raised bump on a distally facing finger to retain a first flange on a syringe cylinder in a ready to use position and a second flange on the syringe cylinder in a protective position.

BRIEF DESCRIPTION OF THE DRAWINGS

These and other features and advantages of the present invention will become appreciated as the same become better understood with reference to the specification, claims and appended drawings wherein:

FIG. 4 shows the start of the relative movement between syringe cylinder and protective cylinder after their release from one another.

FIG. 5 shows the protective position between syringe cylinder and protective cylinder.

FIG. 10 is a cross-sectional side view of an alternative syringe assembly provided in accordance with aspects of the present invention, which comprises a two-part protective cylinder unit.

FIG. 11 is a cross-sectional side view of the protective cylinder of FIG. 10.

FIG. 12 is a cross-sectional side view of the latching ring of FIG. 10, which is configured to latch with the protective cylinder of FIG. 11.

FIG. 13 is an elevation or side view of the protective cylinder of FIG. 11.

FIG. 14 is an elevation or side view of the latching ring of FIG. 12.

FIG. 15 is a cross-sectional side view of an alternative protective cylinder provided in accordance with aspects of the present invention.

FIG. 16 is a cross-sectional side view of an alternative latching ring provided in accordance with aspects of the present invention.

FIG. 17 is a cross-section side view of the protective cylinder of FIG. 15 rotated 90 degrees about an axis defined by the cylinder.

FIG. 18 is a cross-section side view of the latching ring of FIG. 8 rotated 90 degrees about an axis defined by the cylinder.

FIG. 19 is a cross-sectional side view of a protective unit, which comprises the latching ring of FIGS. 16 and 18 latched to the protective cylinder of FIGS. 15 and 17.

FIG. 27-30 show different views of the syringe assembly of FIG. 26.

DETAILED DESCRIPTION

The detailed description set forth below in connection with the appended drawings is intended as a description of the presently preferred embodiments of safety syringes (herein "syringes") provided in accordance with the present invention and is not intended to represent the only forms in which the present invention may be constructed or utilized. The description sets forth the features and the steps for constructing and using the syringes of the present invention in connection with the illustrated embodiments. It is to be understood, however, that the same or equivalent functions and structures may be accomplished by different embodiments that are also intended to be encompassed within the spirit and scope of the invention. As denoted elsewhere herein, like element numbers are intended to indicate like elements or features.

Figure 1:
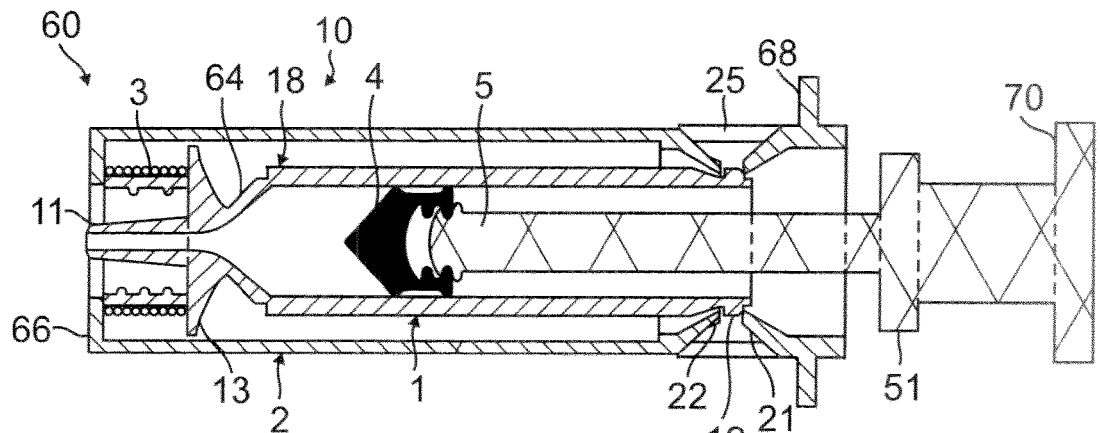
FIG. 1 shows schematically a longitudinal section through a safety syringe in a starting or ready position.

In the figures, 1 designates a syringe cylinder provided at a distal end 60 with a male Luer hub or tip 11 for connecting to a needle hub carrying a needle (not shown). At the proximal end 62, the syringe cylinder is provided with a flange 12 and, in the ready position according to FIG. 1, holding fingers 21 for fixing a protective cylinder 2 that surrounds the syringe cylinder 1 from being displaced by a spring, as further discussed below. The overall syringe assembly is designated by element 10 and the syringe barrel or cylinder 1, plunger rod 5 and plunger tip 4 are collectively referred to herein as a syringe 18.

In one embodiment, the flange 12 is singularly formed with the syringe cylinder 1 by creating two annular grooves distal and proximal of an exterior syringe cylinder section to create the flange. Alternatively, a raised projection may be incorporated to form the flange. Between the Luer hub 11 and a truncated-cone shaped end area 64 of the syringe cylinder 1, a bearing flange 13 is formed, which is used to compress a spring 3 against a radially inwardly projecting shoulder 66, which in one embodiment is an integrally formed flange at a distal end of the protective cylinder 2. The syringe cylinder 1 is held by the elastic holding fingers 21 of the protective cylinder which abut at the flange 12 against the force of the spring 3 in the protective cylinder 2 to prevent relative displacement between the protective cylinder 2 and the syringe cylinder 1.

A plunger 4, sometimes referred to as a plunger tip, is displaceable in the syringe cylinder 1 and is connected to a plunger rod 5, which is provided at the proximal end with a pressure plate 70, also referred to as a pusher flange. Just distal of the pressure plate 70 on the plunger rod 5 is a release flange 51, which is configured to cooperate with the holding fingers 21 on the protective cylinder 2 to release the fingers from the flange 12 on the syringe cylinder to release the spring 3, as further discussed below. In one embodiment, the release flange 51 is integrally formed to the plunger rod 5. However, a skilled artisan can easily modify such feature to produce the same results, such as separately attaching the flange to the plunger rod.

Figure 2:
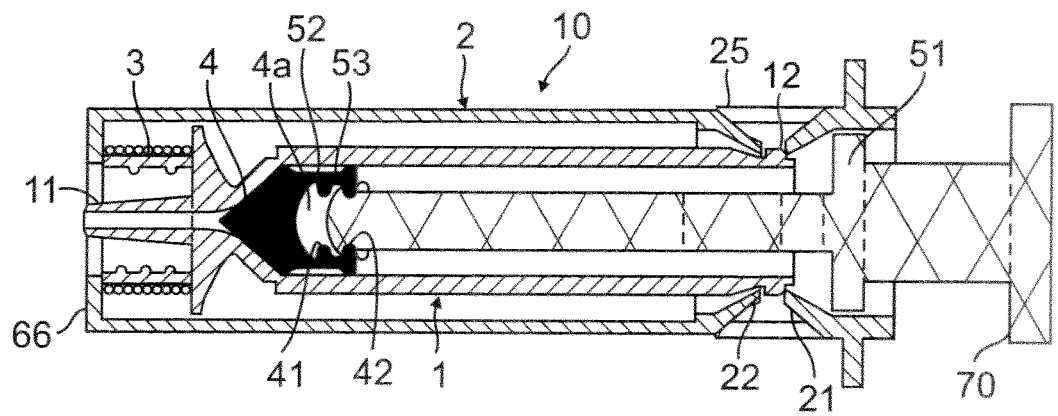
FIG. 2 shows the syringe cylinder in an intermediate position.

At the proximal end of the protective cylinder 2, a flange 68 is formed, which is configured to be gripped or engaged by the fingers to displace the plunger rod 3 inwards (distally) while the pressure plate 70 is displaced into the syringe cylinder 1 by means of the thumb. To put the syringe 10 to use from the ready position shown in FIG. 1, a needle is screwed onto the Luer hub 11 and then the plunger rod advanced distally as shown in FIG. 2. Alternatively, the plunger rod 5 can be advanced first and the needle hub installed onto the Luer tip 11. The plunger rod 5 can then be withdrawn from the syringe cylinder 1 to draw in air into the syringe cylinder. After this, the needle is plunged into a sealed bottle with injection liquid and the syringe is de-aerated. This is accomplished by pushing the plunger rod distally forward while the needle is stuck inside the sealed bottle so that the plunger is displaced into its distal end position as shown in FIG. 2. Injection liquid can now be drawn into the syringe cylinder without negative pressure being generated in the sealed bottle.

However, the user can also stick the syringe into a bottle with injection liquid in the position shown in FIG. 2 and draw up injection liquid. Both methods of drawing in fluid can be carried out without releasing the fingers 21 on the protective cylinder 2 from the flange 12 on the syringe cylinder to allow the spring 3 to expand.

In the position shown in FIG. 2, the syringe is de-aerated because the plunger 4, which is made of elastic material, abuts at the distal front wall of the syringe cylinder 1. By retracting the plunger rod 5 from the syringe cylinder 1, injection liquid can be drawn into the syringe, whereupon an injection can be carried out. At the end of the injection, the plunger 4 is again in abutment at the distal front wall of the syringe cylinder 1, as FIG. 2 shows. In this position, the release flange 51 is still at a slight axial distance away from the holding fingers 21 located on the protective cylinder 2.

The connection between the plunger 4 and the plunger rod 5 is formed telescopically such that a relative movement is possible between the two elements. In the embodiment shown, the plunger 4 has a hollow space 4a, which is open on the proximal side and is provided with two ribs 41, 42 on the inner circumference, which are slightly spaced from one another in the axial direction. The plunger rod 5 is provided at its distal end with two ribs 52 and 53, correspondingly spaced in the axial direction so that the rib 42 of the plunger tip 4 lies between the two ribs 52 and 53 of the plunger rod 5 in FIGS. 1 and 2. The two corresponding sets of ribs permit the plunger tip 4 to be mounted onto the plunger rod 5 yet allow relative movement between the two when the engagement between the two sets of ribs are severed by distal movement of the plunger rod 5, as further discussed below.

Figure 3:
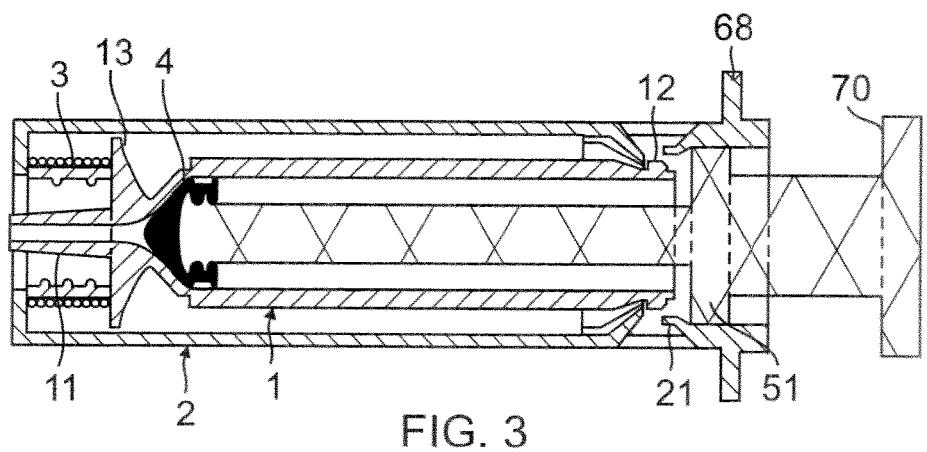
FIG. 3 shows the safety syringe in a release position or activated position in which the connection between the syringe cylinder and the protective cylinder is released or activated.

To release the syringe cylinder 1 from the protective cylinder 2 (or to move the protective cylinder 2 distally relative to the syringe cylinder to shield the needle), the plunger rod 5 is displaced further into the syringe cylinder 1 from the distal end position shown in FIG. 2, wherein the distal end of the plunger rod 5 penetrates further into the plunger tip 4 and the inner circumferential rib 41 of the plunger 4 comes to bear between the circumferential ribs 52 and 53 of the plunger rod, as shown in FIG. 3. By means of this movement of the plunger rod 5 relative to the protective cylinder 2, the release flange 51 displaces or deflects the holding fingers 21 of the protective cylinder 2 radially outwards such that the syringe cylinder 1 is no longer held against the force of the spring 3 in the protective cylinder 2 in the proximal direction. The axial adjustment travel of the release flange 51 to release the holding fingers 21 approximately corresponds to the adjustment travel between the plunger rod 5 into the plunger tip 4.

FIG. 4 shows the position in which the syringe cylinder 1 is somewhat displaced relative to the protective cylinder 2 by the spring 3, after pressure is no longer exerted on the pressure plate 70 and the holding fingers 21 of the protective cylinder 2 no longer engage with the holding flange 12 at the syringe cylinder 1. In this position in FIG. 4, the holding fingers 21 are pivoted radially inwards again due to their elasticity, after no longer being forced apart by the release flange 51, wherein the holding fingers 21 come to bear at an inclined face 14 formed on the distal side of the holding flange 12, so that further displacement of the syringe cylinder 1 relative to the protective cylinder 2 by the spring 3 is not hindered.

FIG. 5 shows the protective position of the safety syringe 10 in which the spring 3 has displaced the syringe cylinder 1 by its distal end up to the proximal end area of the protective cylinder 2. Viewed from a different perspective, the spring 3 has displaced the protective cylinder 2 distally relative to the syringe cylinder 1 so that the needle located at the distal end of the syringe cylinder 1 (not shown) is enveloped completely inside the hollow space 72 of the protective cylinder 2.

In this protective position according to FIG. 5, the proximal side of the bearing flange 13 abuts a shoulder 24 on the inner circumference of the protective cylinder 2 so that the protective cylinder 2 cannot be displaced any further in the distal direction by the spring 3 or the syringe cylinder 1 cannot move any further in the proximal direction relative to the protective cylinder 2. In this position, the blocking fingers 22 formed at the protective cylinder 2 come to bear at a shoulder 15 at the outer circumference of the distal end area of the syringe cylinder 1. As such, relative movement of the syringe cylinder 1 in the distal direction relative to the protective cylinder 2, and thus displacement of the needle out of the protective cylinder 2, is also blocked.

Figure 6:
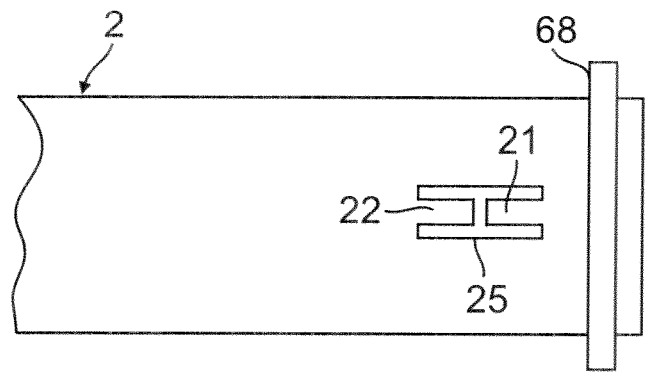
FIG. 6 shows a lateral view of the protective cylinder with holding and blocking fingers.

In the protective position according to FIG. 5, the safety syringe can be disposed of without the risk of accidental needle stick by coming into contact with the used needle. In the exemplary embodiment shown, the elastic holding and blocking fingers 21 and 22 are formed at or moulded onto the protective cylinder 2 in the area of a radial through hole 25 of the protective cylinder 2. FIG. 6 shows a lateral view of the protective cylinder 2 in such an embodiment.

Various modifications of the construction described are possible. For example, in particular, the telescope-type engagement means between plunger tip 4 and plunger rod 5 can be formed in another way, to facilitate displacement of the plunger rod in the distal direction relative to the plunger 4, when the plunger 4 is abutting at the distal front wall of the syringe cylinder 1. Exemplary alternative telescope-type arrangements are disclosed in Ser. No. 11/497,188, filed Jul. 31, 2006, the contents of which are expressly incorporated herein by reference.

Figure 8:
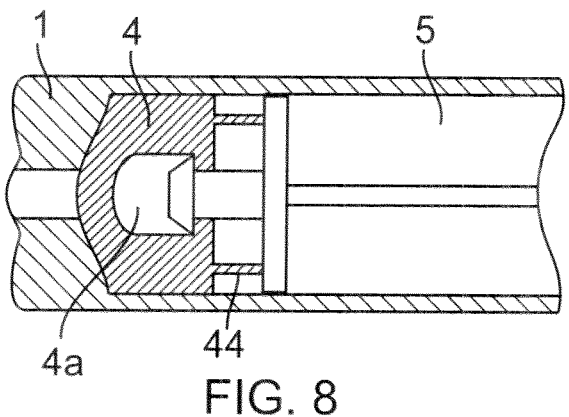
FIGS. 8, 8a, 9 and 9a show alternative embodiments of a plunger, both which being flexible in the axial direction.
Figure 8A:
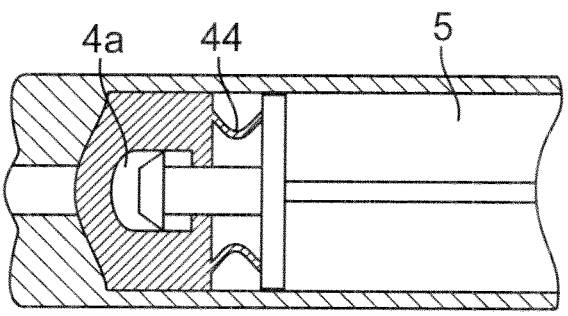

Instead of the described connecting means between the plunger tip 4 and the plunger rod 5, deformable leg extensions 44 can be incorporated on the plunger tip 4 and project in the axial direction, as shown in FIG. 8. The leg extensions 44 are deformable by increased pressure of the plunger rod 5, while the plunger 4 abuts at the distal front wall of the syringe cylinder 1, such that relative movement between plunger 4 and plunger rod 5 is possible for releasing the holding means between the syringe cylinder 1 and the protective cylinder 2. FIG. 8a shows the deformation of the leg extensions 44 at the plunger 4. When the legs are deformed, the plunger rod 5 is allowed to move relative to the plunger tip 4 to thereby allow the release flange 51 to move distally forward to deflect the holding fingers 21.

Figure 9:
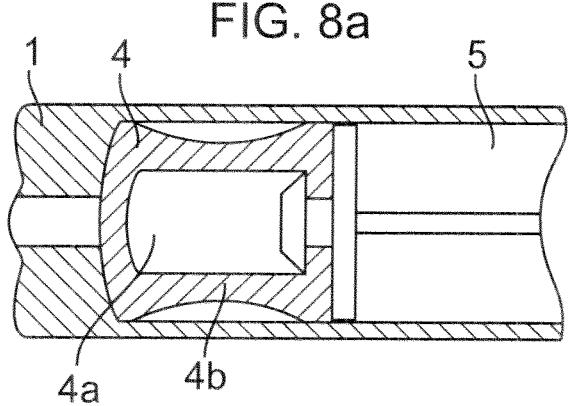
Figure 9A:
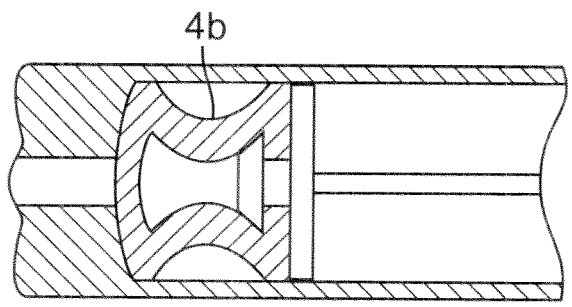

FIG. 9 shows another embodiment of a plunger 4 with a hollow space 4a, whose outer walls 74 are deformable by increased pressure of the plunger rod 5, so that after the plunger 4 abuts at the front wall of the syringe cylinder 1, the plunger rod 5 can carry out a releasing movement in the distal direction relative to the syringe cylinder. FIG. 9a shows the deformation of the plunger 4.

As previously mentioned, the holding flange 12 at the proximal end area of the syringe cylinder 1 is formed by annular recesses in the wall of the syringe cylinder 1, so that the outer diameter of the holding flange 12 corresponds to the outer diameter of the syringe cylinder 1 with recesses formed proximal and distal of the flange. In one embodiment, the recess on the distal side of the holding flange 12 is expediently bevelled in the distal direction at 14 (FIG. 4), so that in the position shown in FIGS. 3 and 4, the holding fingers 21 can slide more easily in the distal direction on the outer circumference of the syringe cylinder 1 and the blocking fingers 22 can abut more closely in the position in FIGS. 1 and 2. It is also possible to form the holding flange 12 projecting from the outer circumference of the syringe cylinder 1 in the radial direction so that no annular recesses are necessary at the syringe cylinder 1.

In a further embodiment, when the plunger 4 abuts at the distal front wall of the syringe cylinder 1, instead of a relative movement between plunger 4 and plunger rod 5, a relative movement between plunger rod 5 and a proximal end portion of the plunger rod is possible, for releasing the connection between syringe cylinder 1 and protective cylinder 2. According to one alternative embodiment, a pressure plate or push plate 70 can be formed with a release flange 51 via a displaceable stop connection, or a spring can be connected to the distal portion of the plunger rod 5, so that when there is increased pressure on the pressure plate 70, the release flange 51 is moved relative to the distal portion of the plunger rod 5 and relative to the protective cylinder 2.

Figure 7:
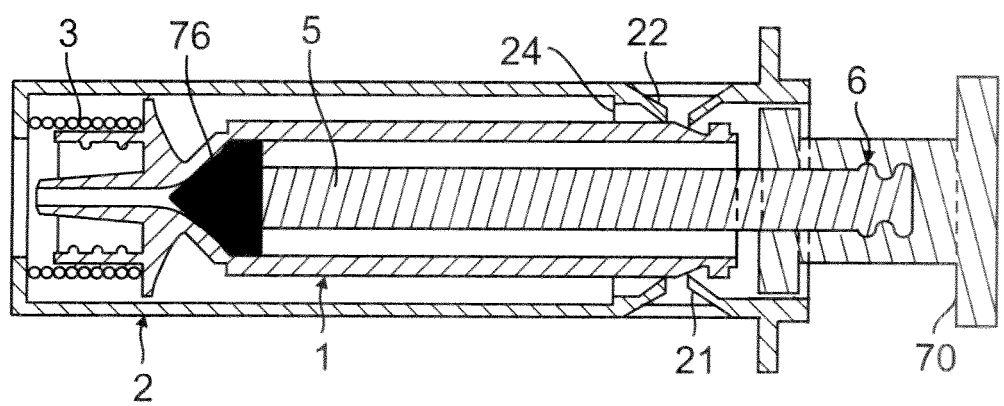
FIGS. 7 and 7a show a schematic presentation of an alternative embodiment, in which the proximal end portion of the plunger rod has sections that telescope relative to one another.

FIG. 7 shows a telescope-type displaceable stop connection 6 between pressure plate 70 with a release flange 51 and a plunger rod 5, similar to the embodiment shown in FIGS. 2 and 3 between plunger 4 and plunger rod 5. In FIG. 7, the plunger tip 76 is fixedly connected to the plunger rod 5, and therefore does not have the configuration according to FIGS. 2 and 3. In other words, in the preferred embodiment of FIG. 7, a compressible plunger chamber is not incorporated.

Figure 7A:
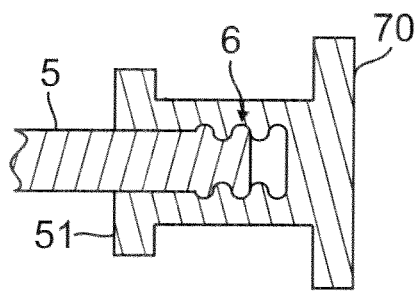

FIG. 7a is a partial cross-sectional side view showing the relative movement between the pressure plate 70 with release flange 51 and the plunger rod 5 corresponding to FIG. 2, wherein the plunger 76 abuts the front wall of the syringe cylinder 1, be it to draw up injection liquid into the syringe cylinder or be it as the end position of the plunger after carrying out an injection. By means of increased pressure on the pressure plate 70 while the plunger 76 abuts the distal front wall of the syringe cylinder 1, the release flange 51 is displaced relative to the plunger rod 5 into the position shown in FIG. 7, which corresponds to FIG. 3. The holding fingers 21 are forced apart by the release flange, so that the spring 3 can move the protective cylinder 2 and the syringe cylinder 1 apart.

Instead of the only schematically shown stop connection 6 between the proximal end of the plunger rod 5 and the release flange 51 moulded onto the pressure plate 70, other embodiments can also be provided, which permit relative movement between plunger rod 5 and pressure plate 70 with release flange 51 during increased pressure on the pressure plate 70. For example, a frangible plate may be used that can tear away upon increased pressure on the pressure plate or push flange 70.

The holding means in the form of holding fingers 21 abutting at the holding flange 12, which is releasable by the plunger rod 5 or by the release flange 51, can also be configured in a different way and can also be separately formed from the blocking means by the blocking fingers 22 projecting in the proximal direction and abutting on the shoulder 15 of the syringe cylinder 1. For example, the blocking fingers 22 or corresponding stops can also be arranged such that they engage the bearing flange 13 at the syringe cylinder 1 on the distal side in the protective position according to FIG. 5, wherein they do not abut at the holding flange 12 in the ready position according to FIG. 1.

To be able to form the protective cylinder 2 from one piece, the distal end of the protective cylinder 2 can be cast without the shoulder 66 which projects radially inwards. After mounting the spring 3 and the syringe cylinder 1 through the open end of the protective cylinder 2, the open end thereof can be flattened down. An alternative is to insert the shoulder 66, which projects radially inwards, as an additional part at the distal end of the protective cylinder 2 after mounting the spring 3 and the syringe cylinder 1, wherein this additional part can be joined to the protective cylinder by welding, bonding or by a snap connection.

Referring now to FIG. 10, across-sectional side view of yet another alternative safety syringe assembly 80 provided in accordance with aspects of the present invention is shown. The present syringe assembly has many similar features as the syringe assembly disclosed with reference to FIGS. 1-4 with the exception of the plunger tip 82 and the latching ring 83. In the embodiment shown, the plunger tip 82 has a wall surface 84 that defines a cavity 4a and an interior annular rib 86 that matingly engages a groove located between a pair of ribs 88, 90 located on a tip career 92. The cavity 4a provides space for accommodating the tip carrier 92 as the same is pushed into the cavity space when the plunger rod 5 is advanced distally after the plunger tip is at its distal end position.

With reference to FIGS. 11 and 12 in addition to FIG. 10, a protective cylinder 94 is shown comprising a radially inward projection shoulder 66 at a distal end 60 and an enlarged skirt section 96 at a proximal end 62 for mating engagement with a latching ring 83. In the embodiment shown, the skirt section 96 has a transition section 98, which marks a line of demarcation between a first internal diameter section 100 and a second larger internal diameter section 102. In one embodiment, the larger second diameter section 102 is sized to accommodate the latching ring 83 so that the internal diameter section 104 of the latching ring can be made equal, somewhat, or nearly equal to the first internal diameter section 100 when the two sections are brought together.

In a preferred embodiment, two openings 106 are incorporated in the skirt section 96. Still more preferably, the two openings 106 are equally spaced around the circumference of the skirt section 96. The openings 106 can have a number of different shapes and sizes, such as square or rectangular, provided they are sufficiently sized and contoured to receive corresponding detents 108 located on the latching ring 83. The detents 108 are so located on the latching ring 83 so as to align with the corresponding two openings 106 on the skirt section 96 to latch thereto. In other embodiments, more than two corresponding sets of openings and detents are incorporated, such as three spaced apart sets and four spaced apart sets.

Two pairs of inclined fingers 21, 22 are located on the latching ring 83. The fingers inclined radially inwardly relative to an axis defined by a lengthwise direction of the latching ring and resemble leaf springs. The fingers may be referred to as distal or first set of fingers and proximal or second set of fingers. The particular name reference is not important and only provided to show that there are two sets of fingers for performing at least two different functions.

FIGS. 13 and 14 are side views of the protective cylinder 94 and latching ring 83 of FIGS. 11 and 12, respectively, rotated approximately 90 degrees about the common axis of the two structures. The detents 108 (only one shown) and the proximal 21 and distal fingers 22 (only one of each shown) are formed on the wall structure 110 of the latching ring 83. Other features may be formed thereon such as markings and labels.

Referring again to FIG. 10 in combination with FIGS. 13 and 14, the safety syringe 80 may be assembled by first placing the latching ring 83 over the proximal end of the syringe cylinder 1, without the plunger rod 5, until the flange 12 on the syringe cylinder is disposed in between the proximal and distal fingers. At this point, or after placing the spring 3 over the threaded shroud 112 at the distal end of the syringe barrel, the plunger rod 5 is inserted into the syringe barrel. Then the protective cylinder 94 is placed over the distal end of the spring and the syringe barrel 1 is advanced distally forward to compress the spring while concurrently latching the detents 108 on the latching ring 83 to the openings 106 of the protective cylinder 94. The syringe assembly is now installed and ready for sterilization and packaging. Alternatively, the spring 3 is first placed inside the protective cylinder 94 then the syringe barrel 1, without the plunger rod, is inserted and advanced distally forward to compress the spring. The latching ring 83 is then assembled until the flange 12 on the syringe cylinder is disposed in between the proximal and distal fingers while concurrently latching the detents 108 on the latching ring 83 to the opening 106 of the protective cylinder 94. Finally, the plunger rod is inserted into the syringe barrel. The syringe assembly 80 may be used in the manner described with reference to the syringe of FIGS. 1-4 to draw in fluid and to inject fluid.

Volumetric markings may be applied on the syringe cylinder 1 to enable a user to read fluid level contained inside the cylinder. Accordingly, in a preferred embodiment, the protective cylinder 94 is made from a transparent thermoplastic material to enable viewing through the wall surface of the protective cylinder.

In a further aspect of the present invention, a method of shielding a needle is described whereby a plunger rod 5 is first advanced until a plunger tip 82 contacts an end surface or distal wall 114 of the syringe barrel to completely discharge any fluid contained inside the syringe cylinder. The plunger rod 5 is then further distally advanced with sufficient force to either compress or distort the plunger tip to cause the interior annular rib 86 of the tip to separate from the gap located between the two ribs 84, 88 on the syringe tip carrier 92. This allows the distal end of the plunger rod to travel into the interior space 4a of the plunger tip. Concurrently therewith, the release flange 51 located on the plunger rod moves forward to deflect the proximal fingers 21 radially outwardly and away from the flange 12 on the syringe cylinder. As the proximal fingers 21 are configured to hold the spring in a compressed position, their deflection radially outwardly permit the spring 3 to expand to push the syringe cylinder proximally or, when viewed from the perspective of the syringe cylinder, push the protective cylinder distally.

The two cylinders move relative to one another until the bearing flange 13 abuts the holding fingers 21. To prevent the syringe assembly 80 from re-setting, i.e., to prevent the syringe cylinder 1 from moving back to its original position so that the syringe can be re-used, the blocking fingers 22 are configured to abut the distal side of the bearing flange 13, on the side that is in contact with the spring 3. The syringe cylinder 1 is then secured in a fixed axial orientation with the protective cylinder 94, similar to the embodiment shown in FIG. 5, notwithstanding possibly some tolerance or slack.

In yet another aspect of the present invention, a method is provided wherein a latching ring 83 comprising proximally and distally facing tangs or fingers 21, 22 is inserted axially into a protective cylinder 94 into mating latching arrangement while the tangs remain outside of the protective cylinder to hold a flange located on a syringe to secure the syringe axially relative to the protective cylinder. In one embodiment, the position of the tangs 21, 22 are located such that even when the plunger tip 82 is advanced distally to contact the distal end wall of the syringe cylinder 1, the holding fingers 21 are not activated to release their hold on the flange 12 of the syringe cylinder 1 thus allowing full de-aeration or injection of fluid without activating the protective cylinder 94 over the needle (such as that shown in FIG. 5).

In a yet further aspect of the present invention, a pair of detents 108 are radially aligned with a pair of proximally and distally facing fingers or tangs 21, 22 to provide visual feedback during assembly of the syringe assembly 80—that the detents 108 are latched to corresponding openings 106 on the protective cylinder and the fingers 21, 22 straddle the flange 12 on the syringe cylinder to axially locate the syringe cylinder relative to the protective cylinder. However, the radial positions of the detents 108 and the fingers 21, 22 along the periphery of the latching ring 83 can vary without deviating from the spirit and scope of the present invention.

Features of the syringe assembly 80 also include a latching ring 83 comprising a cylinder having fingers 21, 22 and detents 108 formed thereon or integrally therewith a gripping flange 68. In one embodiment, the gripping flange 68 is located at a proximal most end of the latching ring 83 and spaced apart from a distal end of the protective cylinder and syringe cylinder. This allows the gripping flange 68 to be gripped during installation of the latching ring to the protective cylinder 94.

Referring now to FIG. 15, a cross-sectional side view of an alternative protective cylinder 120 provided in accordance with further aspects of the present invention is shown. In one embodiment, the protective cylinder 120 comprises a radially inward projection 66 at a distal end 60 and a latching mechanism 122 at a proximal end. In a preferred embodiment, pluralities of teeth or gears 124 are incorporated around the perimeter of the opening defined by the radially inward projection shoulder 66. As further discussed below, the teeth 124 are configured to engage a corresponding set of teeth located on the threaded shroud of a companion syringe cylinder to prevent relative rotation between the protective cylinder 120 and the syringe cylinder during installation of a needle hub onto the male Luer tip of the syringe. In the embodiment shown, the teeth 124 adorn the entire periphery of the opening. However, less number of teeth formed around less than the full circumference of the opening may be practiced without deviating from the spirit and scope of the present invention.

In one embodiment, the latching mechanism 122 comprises a pair of proximally extending latching arms 126, each comprising a detent or barb 128 located thereon for mating connection with a latching ring, as further discussed below. The latching arms 126 are configured to secure the latching ring to the protective cylinder. Thus, an aspect of the present embodiment is a provision for providing a separately formed but subsequently connectable protective cylinder and latching ring to form a protective unit or generically protective cylinder.

With reference now to FIGS. 16-18 in addition to FIG. 15, the protective cylinder 120 further comprises two tines or tangs 130 formed at the proximal end 62 of the cylinder 120. In one embodiment, the tines 130 are formed by molding two channels into the wall surface of the protective cylinder 120. The tines 130 each comprises a raised bump 132 formed on its exterior wall surface, which resembles a partial bead or dome. During assembly when a latching ring 134 is attached to the protective cylinder 120, the interior wall surface 136 of the latching ring forces the two bumps 132 to compress radially inwardly towards the longitudinal axis of the cylinder to then deflect the two tines radially inwardly. More specifically, the inside diameter or the latching ring 134 is approximately equal to the exterior diameter of the protective cylinder. Thus, when the latching ring 134 is slid over the protective cylinder, the ring rides over the two bumps to cause the two tines 130 to deflect radially inwardly. The two tines 130 are configured to function like blocking fingers 22 shown with reference to FIGS. 1-4 and 10.

In one embodiment, the latching ring 134 incorporates an internal shoulder 138 positioned a sufficient distance from an end edge 140 of the latching ring to delimit the amount of insertion or depth that the ring slides over the protective cylinder. Similarly, the two latching arms 126 are sized sufficiently long so that as the ring 134 slides onto the cylinder and is stopped by the shoulder 138, the two arms project through two corresponding locking holes 142 (FIG. 18) located proximate the gripping flange 68 to secure the latching ring to the cylinder. More particularly, the detents 128 located on the two latching arms 126 are configured to engage the locking holes 142 to secure the latching ring to the protective cylinder.

With reference again to FIG. 16 in addition to FIG. 18, two distally facing tangs or tines 144, which are the proximally positioned tines that point distally, are incorporated on the latching ring 134. In one embodiment, the tines 144 are each formed by molding two adjacent channels into the wall surface of the latching ring. In a preferred embodiment, the two tines 144 each has an end edge 146 that is positioned just proximally of a plane defined by the internal shoulder 138. The two tines 144 are also molded with radially inward deflection (FIG. 18) and the relative position of the two end edges 146 relative to the shoulder 138 ensure that the remain radially inwardly deflected and not interfered with by the protective cylinder when the two cylinders are mated together. In a preferred embodiment, the two tines 144 each incorporates a raised bump, similar to the bumps on the proximally facing tangs 130, that are configured to be radially inwardly displaced by the two latching arms 126 when assembled as shown in FIG. 19.

With reference now to FIG. 19, a cross-sectional side view of the latching ring 134 connected to the protective cylinder 120 is shown. The assembled protective unit 145 is configured to be use with a syringe, as further discussed below. In one embodiment, if the cylinder defines a 360-degree radiant, the two tines 130 located on the protective cylinder 120 are located 180 degrees from one another and the two tines 144 located on the latching ring 134 are located 180 degrees from one another. In a preferred embodiment, the four tines 130, 144 are located approximately 90 degrees from one another. However, more than four tines and different angular orientations may be possible without deviating from the spirit and scope of the present invention. Although not shown in FIG. 19, the proximally facing tines 130 on the protective cylinder 120 are deflected radially inwardly by the latching ring 134.

Figure 20:
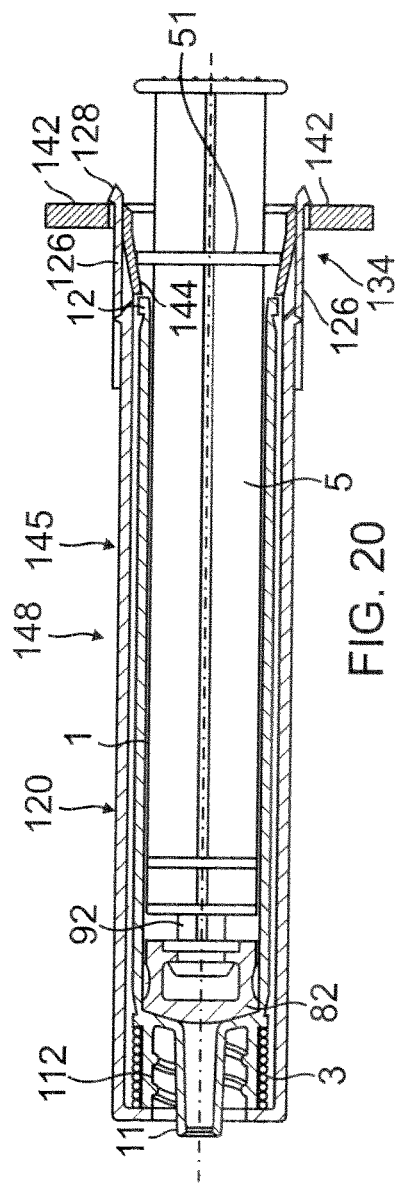
FIG. 20 is a cross-sectional side view of a syringe assembly provided in accordance with aspects of the present invention, which comprises a syringe engaged to the protective unit of FIG. 19.

FIG. 20 is a cross-sectional side view of a syringe assembly 148 provided in accordance with aspects of the present invention. The syringe assembly 148 incorporates the protective unit 145 of FIG. 19 and the syringe of FIG. 10, which includes a syringe cylinder 1, a plunger rod 5 having a plunger tip carrier 92 with a plunger tip 82 mounted thereon, a Luer tip 11, and a compressed spring 3. The syringe assembly 148 may be installed by first sliding the latching ring 134 of FIG. 16 onto the syringe barrel 1 and a spring 3 onto the threaded shroud or collar 112. The spring end of the syringe barrel 1 with the spring 3 is then inserted into the protective cylinder 120 until the two detents 128 on the two latching arms 126 engage the two locking holes 142. In this engagement or latched position, the two tangs 144 on the latching ring 134 abut an end surface of the syringe barrel 1 to limit movement of the barrel 1 proximally, and thereby compress the spring 3. Although not shown in FIG. 20 because they are located orthogonally to the plane of the figure, the proximally facing fingers 130 (FIG. 19) would come to bear against the distal side of the flange 12 on the syringe cylinder 1.

The syringe assembly 148 may be used to connect to a needle hub, draw in fluid, discharge fluid, and activate the protective cylinder 120 over the needle in the same manner and fashion as discussed above with reference to FIGS. 1-5.

Figure 21:
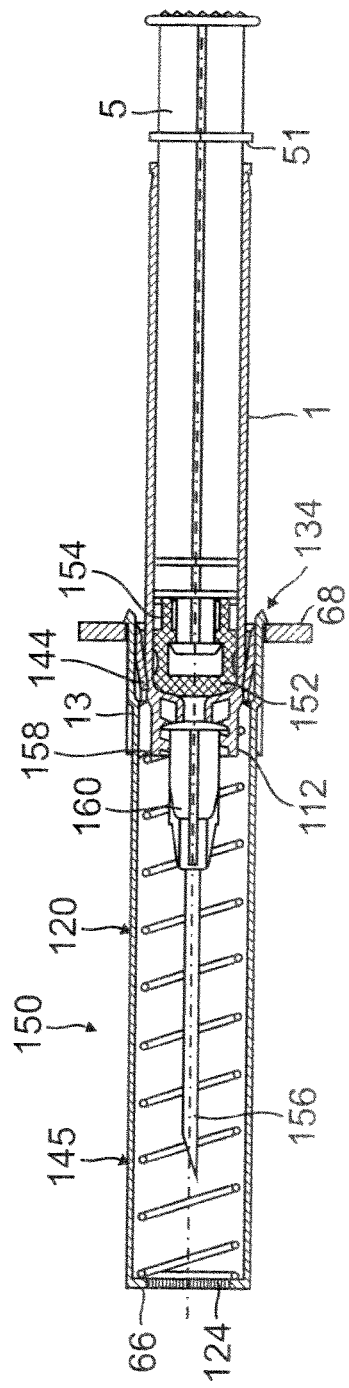
FIG. 21 is a cross-sectional side view of the syringe assembly of FIG. 20 in a protective position.

FIG. 21 is a cross-sectional side view of a syringe assembly 150 in a protective position, which is similar to the syringe assembly 148 of FIG. 20 with at least one additional feature. In the present embodiment, a plunger tip 152 having a pair of leg extensions 134 are incorporated instead of a groove defined by two adjacent ribs, as shown in FIG. 20. The plunger tip 152 therefore resembles the plunger tip shown in FIGS. 8 and 8a. Thus, in the preferred embodiment following discharge of fluid from the syringe, the protective unit 145 does not automatically move relative to the syringe cylinder 1 to shield the needle 156 when the plunger tip 152 contacts the distal wall surface of the syringe cylinder 1. Instead, a distally directed force on the plunger rod of 5 sufficient force is necessary to bend or deflect the leg extensions 154 to thus allow the plunger rod 5 to move a small distance distally to then allow the release flange 51 to deflect the two tangs 144 on the latching ring 134. As previously discussed, when this occurs, the tangs 144 no longer act to resist the spring force, which would allow the spring to expand to move the two cylinders relative to one another. Relative movement between the two is delimited by the tangs 144 abutting the bearing flange 13 on the syringe barrel 1. Although not shown in the cross-sectional side view of FIG. 21, the two tangs or blocking fingers 130 (FIGS. 17 and 19) located on the protective cylinder 120 are configured to abut the distal side of the bearing flange 13 to prevent the syringe cylinder 1 from moving distally relative to the protective cylinder once in the protective position. This feature prevents attempted re-use of the syringe assembly 150.

In a further aspect of the present invention, a method is provided for a syringe assembly wherein two cylinders 1, 145 move relatively to one another after a plunger rod 5 and a plunger tip 152 is caused to move relative to one another by application of a distally directed force following a distal end position of the plunger tip. In a yet further aspect of the present invention, said syringe assembly is made from a two-part protective unit comprising a protective cylinder and a latching ring. Still furthermore, a gripping flange 68 is provided on the latching ring 134 for gripping during use of the syringe assembly.

Figure 22:
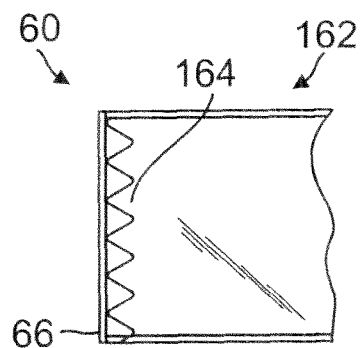
FIG. 22 is a partial side view of a protective cylinder provided in accordance with aspects of the present invention, which shows a plurality of teeth or gears pointing in a proximal direction.
Figure 25:
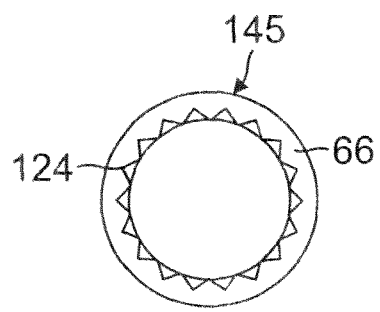
FIG. 25 is an end view of a radially inward projection of a protective cylinder provided in accordance with aspects of the present invention, similar to the cylinder of FIG. 10.

FIG. 22 is a partial elevation or side view of a protective cylinder 162 provided in accordance with aspects of the present invention. The protective cylinder 162 shown is similar to one of the protective cylinders shown herein throughout, including the cylinder 145 shown in FIG. 21, and incorporates holding and blocking fingers at a proximal end (not shown), either as part of the cylinder, part of a latching ring, or both. However, rather than incorporating a gear around a perimeter of the radial inward projection 66 at the distal end 60 of the cylinder as shown in FIG. 25 for engaging with corresponding radially pointing gears 158 on a threaded shroud 112 (See, e.g., FIG. 21), the gear or teeth 164 in the present embodiment extend proximally from near an end of the perimeter of the opening of the radial inward projection 66 to mesh with corresponding distally projecting gears, as further discussed below.

Figure 23:
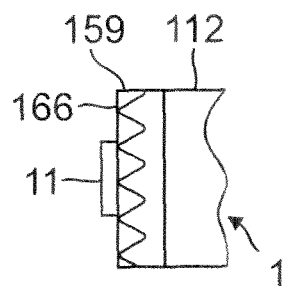
FIG. 23 is a partial side vi of a syringe cylinder provided in accordance with aspects of the present invention, which comprises distally facing gears or teeth for meshing with the gears on the protective cylinder of FIG. 22.

Referring now to FIG. 23, in one embodiment, a companion set of gears or teeth 159 are incorporated on an exterior surface of the threaded shroud 112 of the syringe cylinder 1. The gears or teeth 159 are configured to mate with the gears or teeth 164 located on the radially inward projection shoulder 66 of the protective cylinder 162 (FIG. 22) when the syringe and protective cylinders are coupled in the position shown in FIG. 24. The gear mesh between the two cylinders is configured to secure the two cylinders in a fixed relative rotation so that as a needle hub 160 with a needle 156 (FIG. 21) is mounted over the Luer tip 11 and rotated to engage the threaded shroud 112, the syringe cylinder or the protective cylinder does not also rotate relative to one another.

In one embodiment, the gears 159 are formed by molding the teeth into part of the depth of the wall surface of the threaded shroud 112. In a particular embodiment, the gears 159 are formed near an end edge 166 of the threaded shroud, and more preferably formed such that the tip of each tooth touches an imaginary plane defined by the end edge 166. The gears are further preferably formed to not project radially outwardly away from an axis defined by the syringe, i.e. away from an exterior wall surface of the threaded shroud, so as to allow a spring to be positioned thereon, as shown in FIG. 20.

Figure 24:
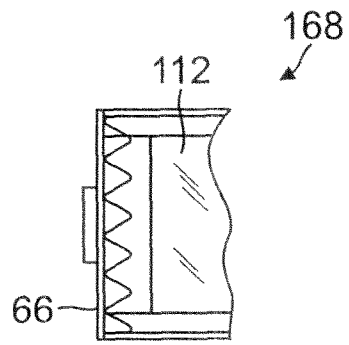
FIG. 24 is a partial side view of a syringe assembly provided in accordance with aspects of the present invention, which comprises the syringe of FIG. 23 inserted into the cylinder of FIG. 22.

Referring now to FIG. 24, a partial side view of a syringe assembly 168 is shown, which comprises the syringe cylinder 1 of FIG. 23 inserted into the protective cylinder 162 of FIG. 22. The protective cylinder 168 is preferably transparent so that volumetric markers, labels, liquid level, and plunger tip position, among other things, may be viewed through the wall surface of the cylinder.

The syringe assembly 168 is shown without a spring for clarity, which normally sits over the threaded shroud 112 as shown in FIG. 20 and compressed by the radial inward shoulder 66 on the protective cylinder 162 and the bearing flange 13 on the syringe cylinder 1. When a needle hub (not shown) is inserted over the Luer tip 11 and rotated to engage the threaded collar or shroud 112, the gears prevent the syringe cylinder 1 from being rotated relative to the protective cylinder.

Thus, in accordance with aspects of the present invention, a method is provided wherein a latching ring (not shown in FIG. 22, see FIGS. 10 and 20) is latched to a protective cylinder to form a protective unit and wherein the protective unit is geared to a syringe cylinder to delimit relative rotation between the two cylinders. In a further aspect of the present invention, there is provided a protective unit comprising a protective cylinder latched to a latching ring comprising a push flange located proximally of a pair of blocking fingers for engaging a proximal end of a syringe, and wherein the protective unit is geared to a syringe cylinder to delimit relative rotation between the two cylinders. In other embodiments, a plunger comprising a release flange located near a push flange and plunger tip comprising a hollow interior is incorporated in any one of the above described syringe assemblies to allow movement of a plunger rod to a distal plunger tip position without activating the fingers with the release flange.

In yet another aspect of the present invention, a method is provided wherein a latching ring 134 comprising distally facing tangs 144 is inserted axially into a protective cylinder 120 in opposing relationship with proximally facing tangs 130. An additional method provided herein is a provision for deflecting two tangs 130 radially inwardly for blocking the bearing flange on the syringe barrel from re-setting. In one embodiment, the tangs are deflected inwardly by compressing a pair of raised bumps 132. In another embodiment, the position of the tangs 130, 144 are located such that even when the plunger tip 82 is advanced distally to contact the distal end wall of the syringe cylinder 1, the distally facing tangs 144 are not activated to release their hold on the flange 12 of the syringe cylinder 1 thus allowing full de-aeration or injection of fluid before activating the protective cylinder 120 over the needle (FIG. 21).

In a yet further aspect of the present invention, a pair of latching arms 126 on the protective cylinder 120 extend into, at least in part, the latching ring 134 and a wall section of the latching ring 134 extend over a proximal end of the protective cylinder 120 to form an assembled protective unit 145. In another embodiment, the detents 128 on the latching arms 126 are configured to extend proximally of a gripping flange 68 on the latching ring 134 to secure the latching ring to the protective cylinder.

Figure 26:
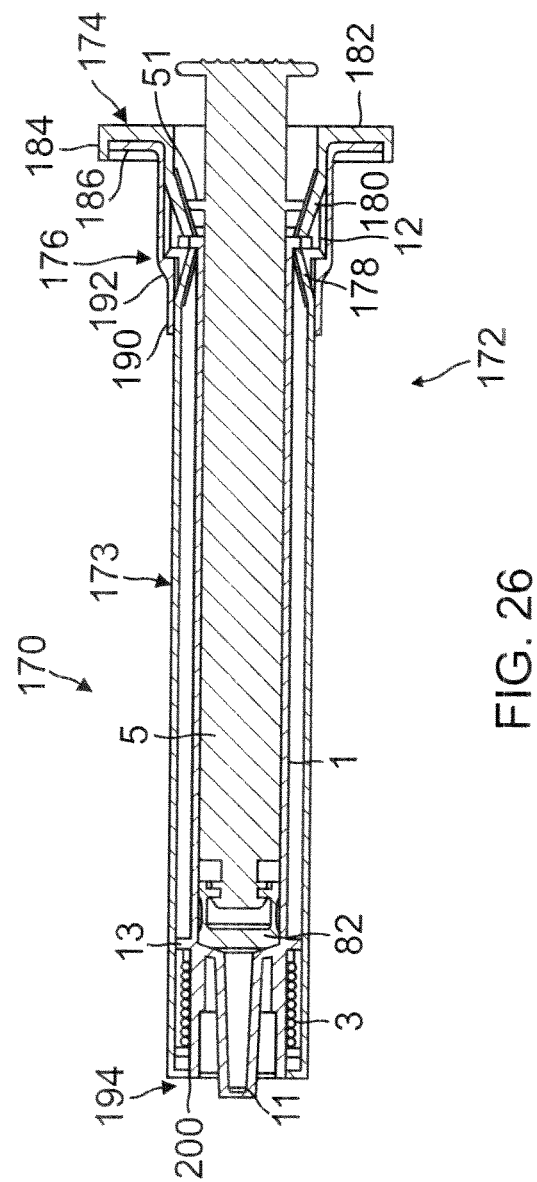
FIG. 26 is a cross-sectional side view of yet another syringe assembly provided in accordance with aspects of the present invention, which comprises a coupler for latching a first cylinder to a second cylinder.

FIG. 26 is a cross-sectional side view of yet another syringe assembly 170 provided in accordance with an alternative aspect of the present invention. The syringe assembly 170 comprises a syringe having a syringe cylinder 1, plunger rod 5, and plunger tip 82 positioned inside an assembled protective unit 172, which comprises a protective cylinder 173 attached to a latching ring 174 by a coupler 176. Two proximally facing fingers 178 are incorporated with the protective cylinder and two distally facing fingers 180 are incorporated with the latching ring 174, for a total of four fingers, to secure the syringe cylinder 1 in axial orientation relative to the protective unit 172, both in an injection ready position or plunger distal position (FIG. 26) and in a protective or shielded position (FIG. 27), as further discussed below. In one embodiment, the proximally facing and distally facing fingers 178, 180 each incorporates a raised bump, similar to the raised bumps 132 shown in FIG. 15, configured to be compressed by the coupler 176 to deflect the fingers radially inwardly when assembled as shown. Less preferred, the fingers may be molded so that they naturally point or slant radially inwardly.

In one embodiment, the latching ring 174 comprises a cylindrical body having the two tangs or fingers 178 formed thereon and a gripping flange 182 located at its proximal end. The gripping flange 182 may embody two extending tabs extending radially outwardly from the cylinder body but more preferably has an oval or oblong shape. In an exemplary embodiment, the gripping flange incorporates a lip 184, which defines a distally facing recessed area 186 for receiving or accommodating a similarly shaped flange 188 located on the coupler 176. To secure the two flanges together, a detent is incorporated on the lip 184 of the gripping flange 182 for securing against the perimeter of the flange 188 of the coupler. In alternative embodiments, the two flanges may be secured together using prior art techniques, such as using adhesive, solvent bond, ultrasonic welding, or dielectric welding.

In one embodiment, the coupler 176 incorporates a body section 190 comprising a raised or transition area 192, which defines a first exterior diameter section distally thereof and a second larger exterior diameter section proximally thereof. Interiorly, a shoulder is formed at the transition area 192 for seating the latching ring 174. The coupler 176 may be secured to the protective cylinder 173 using prior art techniques, such as using adhesive, solvent bond, ultrasonic welding, or dielectric welding.

With reference to FIG. 26 in addition to FIGS. 27-30, in one embodiment, the syringe assembly 170 incorporates an anti-rotation device 194 for preventing relative rotation between the syringe cylinder 1 and the protective cylinder 173 in the injection ready position or plunger distal position (FIG. 26). The preferred anti-rotation device 194 includes a first gear set 196 comprising a plurality of individual gear tooth formed into part of a distal radial shoulder 198 of the protective cylinder 173 (FIG. 28, which is an enlarged view of the distal end of the protective cylinder 173). A distal wall structure or gear bottom land 200 is axially disposed at the base of the first gear set 196 for delimiting distal axial travel of the syringe cylinder 1. The tip 202 of each gear tooth together provide a stop or shoulder for the spring 3. In one embodiment, the first gear set 196 may be molded as a negative of a gear set on a core pin.

With reference now to FIG. 29 (which is an enlarged view of the threaded shroud of the syringe cylinder 1), a second gear set 204 comprising a plurality of individual gear tooth is incorporated on the exterior surface of the threaded shroud 112 of the syringe cylinder 1 for meshing with the first gear set 196, as shown in FIG. 26. In one embodiment, the second gear set 204 is molded into part of the wall thickness of the threaded shroud 112. A wall structure or gear bottom land 206 is located between two adjoining gear teeth. In one embodiment, each gear bottom land comprises generally planar surface having a width that is approximately the same width as the width of each gear tooth.

FIG. 27 is a cross-sectional side view of the syringe assembly 170 of FIG. 26 in a shielded or protective position. In one embodiment, the syringe assembly 170 is placed in the protective position by advancing the plunger rod 5 as shown in FIG. 26 until the plunger tip 82 touches the distal shoulder of the syringe barrel 1 and then further advancing the plunger rod 5 to compress the syringe tip 82. This causes the release flange 51 on the plunger rod 5 to advance axially forward to deflect the distally facing fingers 180 radially outwardly so that the flange 12 on the syringe barrel 1 is no longer retained by the now deflected fingers, which then allows the spring 3 to expand. The spring 3 is allowed to expand until the fingers 180 abut the bearing flange 13 located on the syringe barrel (FIG. 30, which is an exploded view of bubble A of FIG. 27). At the same time, the proximally facing fingers 178 bear against the opposite side of the bearing flange 13 to prevent the syringe barrel 1 from moving back inside the protective cylinder 173. The syringe assembly may also be used in the same manner as described with reference to FIGS. 1-5.

Thus, aspects of the present invention includes a syringe barrel comprising a coupler comprising a cylinder body section configured to compress a raised bump on a proximally facing finger and a raised bump on a distally facing finger to retain a first flange in a ready to use position and a second flange in a protective position. A further aspect of the present invention is a syringe cylinder having proximally and distally facing fingers with raised bumps as described and further having an anti-rotation device for limiting relative rotation between the syringe barrel and the protective cylinder in a ready to use position. In one embodiment, the anti-rotation device includes first and second gear sets each comprising a plurality of individual gear tooth having a gear bottom land having a generally planar surface located between two adjacent gear teeth. In a further aspect of the present invention, the gear bottom land comprises a width of approximately the same width as each gear tooth.

Although limited embodiments of syringes, protective cylinders, protective units, and syringe assemblies and their components have been specifically described and illustrated herein, many modifications and variations will be apparent to those skilled in the art. As examples, two or more projections may be formed on the interior surface of the protective cylinder and the exterior surface of the syringe cylinder to prevent relative rotation, the mating gear set may be incorporated at the proximal ends of the protective cylinder and syringe cylinder, a plunger tip with other than the described engagement to a tip carrier may be incorporated, and the plunger rod may embody two intersecting elongated plates rather than a circular rod. Accordingly, it is to be understood that the protective cylinders, protective units, and syringe assemblies and their components constructed according to principles of this invention may be embodied other than as specifically described herein. Still furthermore, aspects specifically discussed for one structure or cylinder may be used with another structure or cylinder discussed elsewhere herein provided the components or functions are compatible and do not conflict with their intended purposes. The invention is also defined in the following claims.

What is claimed is:

1. A syringe assembly comprising a protective unit comprising a first cylinder of a first length attached to a second cylinder of a shorter second length;
    a coupler attached to the first cylinder;
    a plunger rod comprising a plunger tip positioned inside a syringe cylinder, which is positioned inside the protective unit;
    a pair of proximally facing fingers and a pair of distally facing fingers located on the protective unit comprising a gap therebetween and having a flange on the syringe cylinder positioned in said gap;

a gripping flange having a radially outwardly extending portion and located on the second cylinder and proximally of the proximally facing and distally facing fingers;

wherein a spring is compressed between a portion of the protective unit and a portion of the syringe cylinder, said plunger rod further comprises a release flange for abutting the pair of distally facing fingers located distally of a push flange when the plunger tip contacts a distal wall of the syringe cylinder; and wherein the coupler deflects the proximally facing fingers radially inwardly.

2. The syringe assembly of claim 1, wherein the coupler is attached to the second cylinder.

3. The syringe assembly of claim 1, wherein the first cylinder comprises a pair of latching arms extending into a pair of locking holes located on the gripping flange.

* * * * *

UNITED STATES PATENT AND TRADEMARK OFFICE
CERTIFICATE OF CORRECTION

PATENT NO. : 9,662,456 B2
APPLICATION NO. : 12/595668
DATED : May 30, 2017
INVENTOR(S) : Kevin P. Woehr Page 1 of 1

It is certified that error appears in the above-identified patent and that said Letters Patent is hereby corrected as shown below:

In the Specification

In Column 1, Line 32, delete "no that" and insert -- so that --, therefor.

In Column 3, Line 63, delete "8" and insert -- 18 --, therefor.

In Column 4, Line 11, delete "vi" and insert -- view --, therefor.

In Column 5, Line 1, after "cylinder" insert -- 2, --.

In Column 5, Line 20, delete "3" and insert -- 5 --, therefor.

In Column 8, Line 43, delete "across-sectional" and insert -- a cross-sectional --, therefor.

In Column 8, Line 52, delete "career" and insert -- carrier --, therefor.

In Column 11, Line 37, delete "or" and insert -- of --, therefor.

In Column 12, Line 1, delete "that the" and insert -- that they --, therefor.

In Column 12, Line 54, delete "134" and insert -- 154 --, therefor.

Signed and Sealed this
Eighth Day of January, 2019

Andrei Iancu
*Director of the United States Patent and Trademark Office*